United States Patent
Whitekettle et al.

(10) Patent No.: US 7,785,478 B2
(45) Date of Patent: Aug. 31, 2010

(54) METHOD FOR CONTROLLING PROTOZOA THAT HARBOR BACTERIA

(75) Inventors: Wilson Kurt Whitekettle, Jamison, PA (US); Gloria Jean Tafel, Doylestown, PA (US)

(73) Assignee: General Electric Company, Schenectady, NY (US)

( * ) Notice: Subject to any disclaimer, the term of this patent is extended or adjusted under 35 U.S.C. 154(b) by 428 days.

(21) Appl. No.: 11/835,717

(22) Filed: Aug. 8, 2007

(65) Prior Publication Data

US 2009/0039034 A1    Feb. 12, 2009

(51) Int. Cl.
*C02F 1/50*    (2006.01)

(52) U.S. Cl. .................. 210/764; 422/28; 424/408; 424/417; 514/963

(58) Field of Classification Search .................. 210/764
See application file for complete search history.

(56) References Cited

U.S. PATENT DOCUMENTS

| | | | | |
|---|---|---|---|---|
| 4,561,981 A | * | 12/1985 | Characklis | 210/696 |
| 5,164,096 A | * | 11/1992 | Nunn | 210/754 |
| 5,547,939 A | * | 8/1996 | Selsted | 514/14 |
| 6,579,541 B2 | * | 6/2003 | Antelman | 424/646 |
| 6,579,859 B1 | | 6/2003 | Whitekettle | |
| 6,811,711 B2 | * | 11/2004 | Unhoch et al. | 210/755 |
| 6,998,049 B1 | * | 2/2006 | Meyer et al. | 210/632 |
| 2005/0027010 A1 | | 2/2005 | Whitekettle | |
| 2005/0080142 A1 | | 4/2005 | Whitekettle | |

FOREIGN PATENT DOCUMENTS

WO    2005/020684 A    3/2005
WO    2005/027639 A    3/2005

OTHER PUBLICATIONS

Jones, Malcolm, Biofilms and Antibiotic Therapy, Advanced Drug Delivery Reviews, Jun. 13, 2005, pp. 1539-1550, vol. 57, Elsevier B.V., United Kingdom.
Smith, Anthony W., Use of Liposomes to Deliver Bactericides, Methods in Enzymology, 2005, pp. 211-218, vol. 391, Elsevier, Inc., United Kingdom.
PCT/US2008/065047 Search Report.

* cited by examiner

*Primary Examiner*—Peter A Hruskoci
(74) *Attorney, Agent, or Firm*—GE Global Patent Operation; Barbara A. Toop; Catherine J. Winter

(57) ABSTRACT

A method for controlling protozoa trophozites and cysts wherein biocides or control agents are encapsulated within microcapsules or manufactured into the core of liposomes, thereafter the biocide containing microcapsules or liposomes are then introduced into an aqueous system.

19 Claims, No Drawings

METHOD FOR CONTROLLING PROTOZOA THAT HARBOR BACTERIA

FIELD OF THE INVENTION

The field of the invention relates to methods for controlling protozoa trophozoites and cysts that carry or harbor bacteria in aqueous systems. More particularly, embodiments of the present invention relate to methods for controlling bacteria engulfed within protozoa in the amoeboid form, including the bacterium *Legionella pneumophila*.

BACKGROUND OF THE INVENTION

Intracellular bacterial pathogens, that is bacterial pathogens that inhabit another cell or microorganism, are a major cause of human morbidity and mortality. Evading hostile intracellular environments is one of the ways pathogens can live within a host cell, grow symbiotically or parasitically within host cells, and yet not be killed or inhibited by the host cell. These parasites have developed ways of interacting and overcoming the host cells natural defense mechanisms.

*Legionella pneumophila*, a bacterium known to cause Legionnaire's Disease and Pontiac fever in humans is a parasite of this type. While the *Legionella* cells can be killed readily if exposed to certain chemical agents and antibiotics, *Legionella* can also be found engulfed (phagocitized) within certain protozoa hosts. *Legionella* are often found in biofilms adsorbed to solid surfaces in, for example, water distribution systems, cooling towers, showers, aquaria, sprinklers, spas, and cleaning baths. Protozoa are natural grazers on surfaces and engulf and digest bacteria as part of their natural life cycle. In most cases, the protozoa digest these bacteria through the use of digestive enzymes in their phagosomes (digestive vacules). In the case of *Legionella*, however, this is not the case. The protozoa are not readily capable of degrading the engulfed *Legionella* cells, and in fact the *Legionella* grow and increase their numbers while protected within protozoa phagosomes. Legionellosis in humans can be contracted by breathing *Legionella* aerosols containing either the free-living bacterial cells or by inhaling aerosols of *Legionella* concentrated within susceptible protozoa. A *Legionella* control agent, therefore, must be capable of killing free-living *Legionella*, *Legionella* within protozoa, or the protozoa themselves. The agents described in this invention are capable of killing the free-living *Legionella* and the host protozoa. Two protozoa species capable of harboring infectious *Legionella* are *Acanthamoeba* and *Tetrahymena*.

In order to effectively control *Legionella*, in addition to killing the free living or protozoa an additional factor must be taken into account. Certain protozoa, particularly amoeboid forms, have evolved mechanisms for surviving in hostile environments. Examples of hostile environments are high temperature, desiccation, presence of chemical agents/antibiotics, lack of food sources, etc. Upon encountering a hostile environment, these protozoa revert to a cyst form that is very difficult to kill. The cyst form becomes much less susceptible to chemical agents that readily kill the same organism when it is in non-cyst (trophozoite) form. Introduction of a chemical control agent to eliminate *Acanthamoeba* can actually provide the hostile environment to which the protozoa responds by reverting to a cyst form, thereby rendering it invulnerable to the chemical agent. When the cyst contains the pathogen *Legionella*, the chemical agent can no longer reach the engulfed bacteria, and the chemical treatment is rendered ineffective. As an example, chlorination or bleach is considered essential to control *Legionella* in water distribution systems. Exposed *Legionella* are readily killed by low levels of free chlorine (0.2-0.5 µg/ml).

Infective *Legionella* can also be contained in *Acanthamoeba* phagosomes if those protozoa are present. The *Acanthamoeba*, sensing the chlorine presence, reverts to a cyst form, inadvertently preserving and protecting the *Legionella* parasites engulfed within it. The *Acanthamoeba* cysts treated with >500 times (>100 µg/ml "free" chlorine) the concentration needed to kill the trophozoite forms are not killed in the cyst form. The cysts can revert to the active trophozoite form upon removal of the oxidant.

Currently there are no known cyst deactivating agents in commercial use at this time. Although control agents or biocides which effectively kill or treat the *Legionella* bacteria are known, there is no method currently in use which provides for the means to effectively introduce the biocides or control agents into the water systems where the *Legionella* bacteria and *Legionella* harboring protozoa and cysts reside. Control agents that kill the *Legionella* harboring protozoa and protozoan cysts provide a much needed additional tool to safeguard the health of workers and the public against the respiratory pneumonias which can result from inhalation of *Legionella* or *Legionella*-containing protozoa cysts. For example, U.S. Pat. No. 6,579,859 discloses the use of phosphonium salts of the general formula $(R_1)_3P^+R_2.X^-$ wherein $R_1$ is an alkyl group of from 1 to 8 carbon atoms, $R_2$ is an n-alkyl group giving 8 to 20 carbon atoms and X is an anion consisting of a halide, sulfate, nitrate, nitrite, etc.

US patent publication no. 2005/002710 teaches the exposure of the protozoa to quaternary ammonium salts, while US patent publication no. 2005/0080142 discloses the use of guanidine or biguanidine salts to control *Legionella* type bacteria in the free-living state as well as when engulfed in the trophozoite form or *Acanthamoeba* in cyst form.

However, the method of introducing these agents to the *Legionella* bacteria has been a barrier, particularly under actually working conditions. Therefore, a need still exists for a means to take the known biocide agents, such as those cited above, and put them in contact with the *Legionella* bacteria in a way that is efficient and effective, and will be of commercial use.

SUMMARY OF THE INVENTION

An embodiment of the present invention comprises a method for controlling protozoa trophozites and cysts wherein one or more biocides or control agents are encapsulated within a microcapsule and then introduced into an aqueous system.

According to another embodiment of the invention, liposomes are manufactured with a biocide or control agent contained within the aqueous liposome core or within the hydrophobic liposome membrane, and then these liposomes are introduced into an aqueous system to control protozoa trophozites or cysts.

The various features of novelty which characterize the invention are pointed out with particularity in the claims annexed to and forming a part of this disclosure. Changes to and substitutions of the various components of the invention can of course be made. The invention resides as well in sub-combinations and sub-systems of the elements described, and in methods of using them.

DETAILED DESCRIPTION OF THE INVENTION

While the present invention is described herein with references to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but all that fall within the scope of the appended claims.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus.

The present invention relates to methods for controlling protozoa trophozoites and cysts that carry or harbor bacteria in aqueous systems. More particularly, embodiments of the present invention relate to methods for controlling bacteria engulfed within protozoa in the amoeboid form, including the bacterium *Legionella pneumophila*.

Applicants' realization underlying the invention is that since the *Legionella* bacteria are engulfed and protected within the phagosomes of the protozoa, a *Legionella* killing agent, biocide, or control agent must be placed inside the protozoa, in close proximity to the *Legionella* cells without causing the protozoa to grow into a cyst stage. An alternate embodiment provides for the introduction of a biocide or agent that would appear benign to the protozoa and induce them to excyst or revert back to an active trophozoite form. "Biocides" is intended to include, but not be limited to biocides, biocide compositions, killing agents, control agents, and combinations thereof.

One embodiment provides a method for controlling protozoa trophozites and cysts which comprises encapsulating a biocide, killing agent or control agent in a micro-capsule or nano-capsule, and then introducing the micro-capsule or nano-capsule into an aqueous system in effective amounts. The microcapsules or nano-capsules are produced and applied in effective sizes, that is of a size to be phagocytized by protozoa, such as from about 0.025 to about 10 microns. The micro-capsule or nano-capsule is produced such that is has an exterior composition adapted for digestion by said protozoa. Aqueous systems include, but are not limited to, water distribution systems, cooling towers, showers, aquaria, sprinklers, spas, and cleaning baths. An alternate or further embodiment provides for manufacturing liposomes such that a biocide or agent is contained within the aqueous liposome core or trapped within the hydrophobic lipid layers. Thereafter, the liposomes are introduced into an aqueous system. The liposomes may be the encapsulating bodies containing the biocide, or such a biocide-containing liposomes may themselves be further encapsulated, e.g., by a thin shell of protective material. In the latter case, the shell may, for example, be compounded to provide a further, temporary protective cover for the liposome, such as a degradable skin, that enhances the lifetime of the liposome in the water system yet dissolves, decays or otherwise breaks down after a certain time, or under certain conditions, releasing the liposomes which may then act on the target organisms.

Effective amounts of the biocide containing microcapsule or liposome is introduced into an aqueous system containing infected protozoa. The active protozoa, the trophozoite stage, then grazes on the microcapsules or liposomes, mistaking them for bacteria cells. Once incorporated into the protozoan cells, i.e. once they have been phagocitized, the natural enzymatic breakdown of the biocide containing microcapsule or liposome by the protozoa would result in the release of the biocide, killing agent or control agent in high concentration in the protozoa, in direct proximity to the engulfed *Legionella*. Rapid *Legionella* death would then proceed. The benign surface structure of the microcapsule or liposome is additionally advantageous in that, unlike a traditional control agent, it should not induce cyst formation, creating more barriers to treatment. In general, the ability of encapsulated control agents to specifically be taken up by and target the protozoa, is expected to allow a relatively low concentration of treatment material to be added to a fluid system yet be more highly effective than the use of free biocide, whose efficacy depends on its level in the fluid as a whole. Effective amounts of the biocide containing microcapsule or liposome would depend on the biocide or agent incorporated therein. However effective amounts include from about 0.05 to about 500 micrograms per milliliter, or alternately about 0.1 to about 100 micrograms per milliliter.

This method would also lead to the destruction of the host protozoa by the biocide or agent. In the event that the protozoa are already in the cyst stage, the addition of liposomes or microcapsules prepared with bacterial cell size and suitable membrane characteristics should induce the cysts to excyst or revert to active trophozoite stage in order to take advantage of the new food source. At that point, grazing and engulfing of the liposomes by the protozoa would then occur as set forth above.

Liposomes, which are systems in which lipids are added to an aqueous buffer to form vesicles, structures that enclose a volume, may be manufactured by any known process. Such processes may employ, but are not limited to, injection, extrusion (for example pressure extrusion of an aqueous biocide through a porous membrane into the lipid body or vice-versa), sonication, microfluid processors and rotor-stator mixers. The biocide containing liposomes should be produced in sizes that mimic bacterial cells, from about 0.05 to about 15μ, or alternately, about 0.1 to 10.0μ. Similarly, the agent may encapsulated within other oil or oil-like phases by known encapsulation processes, so as to have one or more protective outer layers that define the microcapsule lifetime, delivery characteristics and use environment.

Any available biocide or killing agent could be used in the present methods, including, but not limited to guanidine or biguanidine salts, quaternary ammonium salts and phosphonium salts. Examples of guanidine or biguanidine salts are of the general formulas

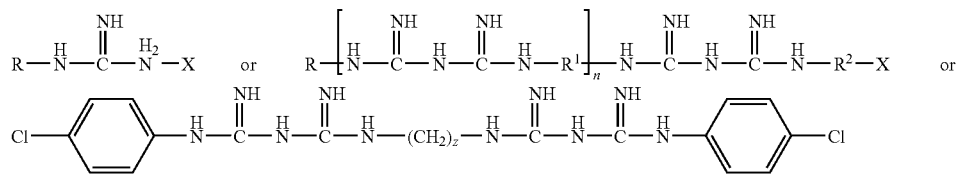

wherein R, $R^1$, $R^2$ are independently H, $C_1$-$C_{20}$ substituted or non-substituted alkyl (linear or branched) or aryl, X is an organic or inorganic acid, n is 0-20 and z is 1-12.

Examples of the general formula of acceptable phosphonium salts comprises $(R_1)_3P^+R_2.X^-$ wherein $R_1$ is an alkyl group of from 1 to 8 carbon atoms, $R_2$ is an n-alkyl group giving 8 to 20 carbon atoms and X is an anion consisting of a halide, sulfate, nitrate, nitrite, and combinations thereof.

An alternative formula provides that $R_1$ is an alkyl group having from 1-8 carbons, $R_2$ is an n-alkyl group having 6-20 carbon groups and $X^-$ is an anion such as halides, sulfates, nitrates, nitrites and mixtures thereof Preferably, $X^-$ is chloride, bromide, iodide, $SO_4^=$, and $NO_3^-$, $NO_2^-$ or mixtures thereof.

Another embodiment provides R1 and R2 are hydroxyalkyl groups having from 1-4 carbons and $X^-$ is an anion such as halides, sulfates, nitrates, nitrites and mixtures thereof Preferably, $X^-$ is chloride, bromide, iodide, $SO_4^=$, and $NO3^-$, $NO2^-$ or mixtures thereof.

Quaternary ammonium salts are another example of a biocide or agent that may be encapsulated or manufactured into a liposome core, and are of the general formula

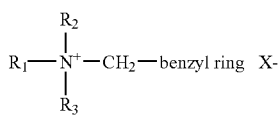

wherein $R_1$ is an n-alkyl group of chain length $C_8$-$C_{18}$; $R_2$ and $R_3$ are $CH_3$ or n-alkyl group of chain length $C_2$-$C_8$ and $X^-$ is an anion such as halides, sulfates, nitrates, nitrites and mixtures thereof.

An alternate embodiment of this invention provides for a method for controlling other bacterial species, or infection carrying protozoa, including but not limited to those that result in amoebic dysentery, malaria, Giardiasis, Trichomoniasis, Cryptosporidiosis and other pathogenic protozoa. Additionally, the biocide containing liposomes or microcapsules can be used in a troubleshooting or proactive measure, by treating non-infected aqueous systems to be ready to attack as soon as the infected protozoa begin to appear in infective numbers.

While the present invention has been described with references to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but all that fall within the scope of the appended claims.

What is claimed is:

1. A method of destroying protozoa trophozites and cysts that carry or harbor bacteria in an aqueous system comprising encapsulating a biocide in a micro- or nano-capsule having an exterior composition adapted for digestion by said protozoa, and introducing the biocide containing micro- or nano-capsules into said aqueous system, wherein the amount of the biocide introduced into the aqueous system is from about 0.05 to about 500 micrograms per milliliter, and wherein said protozoa digests and engulfs the micro- or nano-capsule, which places the biocide inside the protozoa to destroy said protozoa and bacteria, without causing the protozoa to revert back to a cyst form.

2. The method of claim 1 wherein said protozoa are in the trophozoite form.

3. The method of claim 1 wherein said protozoa are in the cyst form.

4. The method of claim 1 wherein said protozoa contain *Legionella* type bacteria.

5. The method of claim 1 wherein the biocide is chosen from the group consisting of biocide compositions, killing agents and combinations thereof.

6. The method of claim 1 wherein the capsules are produced and applied in sizes from about 0.025 to about 10 microns.

7. The method of claim 1 wherein the biocide is chosen from the group consisting of guanidine or biguanidine salts, quaternary ammonium salts and phosphonium salts.

8. The method of claim 1 wherein the effective amount of the biocide introduced into the aqueous system is from about 0.1 to about 100 micrograms per milliliter.

9. The method of claim 1 wherein the aqueous system is chosen from the group consisting of potable and non-potable water distribution systems, cooling towers, showers, aquaria, sprinklers, spas, pipelines, and cleaning baths.

10. The method of claim 1 wherein the micro-capsule or nano-capsule is of a size to be phagocytized by protozoa.

11. A method of destroying protozoa trophozites and cysts that carry or harbor bacteria in an aqueous system comprising manufacturing a liposome having a diameter of from about 0.025 to about 15 microns and which incorporates a biocide in its core, and is adapted for enzymatic breakdown by the protozoa and introducing the biocide containing liposomes into said aqueous system, wherein the amount of the biocide introduced into the aqueous system is from about 0.05 to about 500 micrograms per milliliter, and wherein said protozoa enzymatically breaks down and engulfs the liposome, which places the biocide inside the protozoa to destroy said protozoa and bacteria, without causing the protozoa to revert back to a cyst form.

12. The method of claim 11 wherein said protozoa are in the trophozoite form.

13. The method of claim 11 wherein said protozoa are in the cyst form.

14. The method of claim 11 wherein said protozoa contain *Legionella* type bacteria.

15. The method of claim 11 wherein the biocide is chosen from the group consisting of biocide compositions, killing agents and combinations thereof.

16. The method of claim 11 wherein the liposomes are produced and applied in diameter sizes from about 0.025 to about 10 microns.

17. The method of claim 11 wherein the biocide is chosen from the group consisting of guanidine or biguanidine salts, quaternary ammonium salts and phosphonium salts.

18. The method of claim 11 wherein the effective amount of the biocide introduced into the aqueous system is from about 0.1 to about 100 micrograms per milliliter.

19. The method of claim 11 wherein the aqueous system is chosen from the group consisting of potable and non-potable water distribution systems, cooling towers, showers, aquaria, sprinklers, spas, pipelines and cleaning baths.

* * * * *

UNITED STATES PATENT AND TRADEMARK OFFICE
CERTIFICATE OF CORRECTION

| | | |
|---|---|---|
| PATENT NO. | : 7,785,478 B2 | Page 1 of 1 |
| APPLICATION NO. | : 11/835717 | |
| DATED | : August 31, 2010 | |
| INVENTOR(S) | : Whitekettle et al. | |

It is certified that error appears in the above-identified patent and that said Letters Patent is hereby corrected as shown below:

In Column 5, Line 24, delete "$SO_4^=$," and insert -- $SO_4^{2-}$, --, therefor.

In Column 5, line 29, delete "$SO_4^=$," and insert -- $SO_4^{2-}$, --, therefor.

Signed and Sealed this
Tenth Day of May, 2011

David J. Kappos
*Director of the United States Patent and Trademark Office*